United States Patent [19]
Bryant et al.

[11] Patent Number: 5,482,958
[45] Date of Patent: Jan. 9, 1996

[54] METHOD FOR TREATING ENDOMETRIOSIS

[75] Inventors: Henry U. Bryant; Jeffrey A. Dodge, both of Indianapolis, Ind.

[73] Assignee: Eli Lilly and Company, Indianapolis, Ind.

[21] Appl. No.: 419,312

[22] Filed: Apr. 10, 1995

Related U.S. Application Data

[62] Division of Ser. No. 330,755, Oct. 28, 1994, which is a division of Ser. No. 198,456, Feb. 18, 1994, Pat. No. 5,407,955.

[51] Int. Cl.$^6$ .......................... A61K 31/54; A01N 43/36
[52] U.S. Cl. .................. 514/408; 514/233.5; 514/320; 514/253; 514/456
[58] Field of Search ........................ 514/456, 233.5, 514/320, 253, 408

[56] References Cited

U.S. PATENT DOCUMENTS

| | | | |
|---|---|---|---|
| 3,340,276 | 9/1967 | Carney et al. | 260/345.2 |
| 3,535,344 | 10/1970 | Irmscher et al. | 260/345.2 |
| 3,882,287 | 7/1974 | Bolger et al. | 260/326.5 |
| 4,945,086 | 7/1990 | Benitz et al. | 514/56 |
| 4,988,735 | 1/1991 | Casagrande et al. | 514/648 |
| 5,280,040 | 1/1994 | Labroo et al. | 514/456 |
| 5,283,257 | 2/1994 | Gregory et al. | 514/458 |
| 5,389,646 | 2/1995 | Labroo | 514/456 |
| 5,395,842 | 3/1995 | Labrie et al. | 514/456 |
| 5,407,947 | 4/1995 | Bryant et al. | 514/320 |
| 5,446,061 | 8/1995 | Bryant et al. | 514/456 |

*Primary Examiner*—Marianne M. Cintins
*Assistant Examiner*—Keith MacMillan

*Attorney, Agent, or Firm*—Steven A. Fontana; David E. Boone

[57] ABSTRACT

The present invention provides novel methods of lowering serum cholesterol and inhibiting smoother muscle cell proliferation, particularly restenosis, in humans, and inhibiting uterine fibroid disease and endometriosis in women comprising administering to a human/woman in need of treatment an effective amount of a compound of formula I

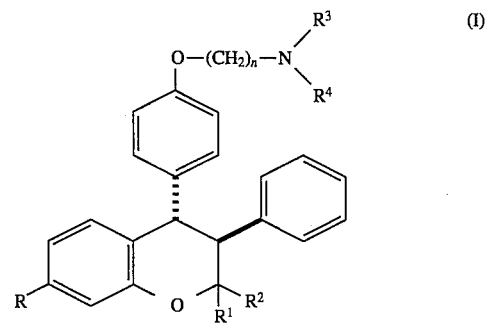

wherein
R is $C_1$–$C_6$ alkyl, $C_1$–$C_6$ alkoxy, halo, or trifluoromethyl;
$R^1$ and $R^2$ each are the same or different $C_1$–$C_6$ alkyl group;
n is an integer from 2 to 6; and
$R^3$ and $R^4$ each are independently $C_1$–$C_4$ alkyl, or combine to form a substituent selected from the group consisting of pyrrolidino, morpholino, piperidino, piperazino, 4-($C_1$–$C_6$ alkyl)piperazino, and 4-phenyl-piperazino;
or a pharmaceutically acceptable salt thereof.

4 Claims, No Drawings

METHOD FOR TREATING ENDOMETRIOSIS

This application is a division of application Ser. No. 08/330,755, filed Oct. 28, 1994, which is a division of prior application Ser. No. 08/198,456, filed Feb. 18, 1994, now U.S. Pat. No. 5,407,955.

BACKGROUND OF THE INVENTION

The present invention relates to the discovery that a group of 3,4-(diphenyl)chromans are useful for lowering serum cholesterol and inhibiting smooth muscle cell proliferation, particularly, restenosis, in humans, and inhibiting endometriosis and uterine fibroid disease in women.

All mammalian cells require cholesterol as a structural component of their cell membranes and for non-sterol end products. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins (LDL'S) have been demonstrated to be a major contributing factor in the development and progression of atherosclerosis.

Estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer and possibly breast cancer, causing many women to avoid this treatment. Recently suggested therapeutic regimens which seek to lessen the cancer risk, such as administering combinations of progestin and estrogen, cause the patient to experience unacceptable bleeding. Furthermore, combining progestin with estrogen seems to blunt the serum cholesterol lowering effects of estrogen. The significant undesirable effects associated with estrogen therapy support the need to develop alternative therapies for hyperlipidemia/hypercholesterolemia that have the desirable effect on serum LDL but do not cause undesirable effects.

Attempts to fill this need by the use of compounds commonly known as antiestrogens which interact with an estrogen receptor and/or bind with what has been termed the antiestrogen binding site (AEBS) have had limited success, perhaps due to the fact that these compounds generally display a mixed agonist/antagonist effect and are subject to the same adverse effects associated with estrogen therapy.

The present invention provides methods for lowering serum cholesterol levels without the associated adverse effects of estrogen therapy, and thus, provides an effective and acceptable treatment for hyperlipidemia/hypercholesterolemia.

Smooth muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase, occurring hours to days after PTCA, is due to thrombosis with some vasospasms while the late phase appears to be dominated by excessive proliferation and migration of smooth muscle cells. In this disease, the increased cell motility and colonization by smooth muscle cells and macrophages contribute significantly to the pathogenesis of the disease. The excessive proliferation and migration of vascular smooth muscle cells may be the primary mechanism to the reocclusion of coronary arteries following PTCA, atherectomy, laser angioplasty, and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology* 8:369–375 (August 1985).

Vascular restenosis remains a major long term complication following surgical intervention of blocked arteries by percutaneous transluminal coronary angioplasty (PTCA), atherectomy, laser angioplasty, and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment anti prevention of vascular restenosis. See "Prevention of Restenosis after Percutaneous Transluminal Coronary Angioplasty: The Search for a 'Magic Bullet'," Hermans et al., *American Heart Journal* 122:171–187 (July 1991).

In the pathogenesis of restenosis, excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth muscle cells are useful in the treatment and prevention of restenosis. The present invention provides for the use of compounds as smooth muscle cell proliferation inhibitors.

Unterine fibroid disease (uterine fibrosis) is an old and ever present clinical problem which goes under a variety of names, including uterine hypertrophy, uterine lieomyomata, myometrial hypertrophy, fibrosis uteri, and fibrotic metritis. Essentially, uterine fibroid disease is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibroid disease involves surgical procedures which are both costly and sometimes a source of complications such as the formation of abdominal adhesions and infections. In some patients, initial surgery is only a temporary treatment and the fibroids regrow. In those cases, a hysterectomy is performed which effectively ends the fibroids, but also the reproductive life of the patient. Also, gonadotropin releasing hormone antagonists may be administered, but their use is tempered by the fact they can lead to osteoporosis.

Endometriosis is a condition of severe dysmenorrhea, which is accompanied by severe pain, bleeding into the endometrial masses or peritoneal cavity, and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release, and subsequent ovarian production of estrogen. However, it is sometimes necessary to use continuous estrogen to control the symptoms. This use of estrogen can often lead to undesirable side effects and even the risk of endometrial cancer.

Another treatment consists of continuous administration of progestin which induces amenorrhea and, by suppressing ovarian estrogen production, can cause regressions of the endometrial growths. The use of chronic progestin therapy is often accompanied by the unpleasant central nervous system side effects of progestin, and often leads to infertility due to suppression of ovarian function.

A third treatment consists of the administration of weak androgens, which are effective in controlling the endometriosis. However, they induce severe masculinizing effects. Several of these treatments have also been implicated in causing a mild degree of bone loss with continued therapy.

Therefore, new methods of treating endometriosis are desirable.

SUMMARY OF THE INVENTION

The present invention relates to methods for lowering serum cholesterol and inhibiting smooth muscle cell proliferation and restenosis comprising administering to a human in need of treatment an effective amount of a compound of formula I

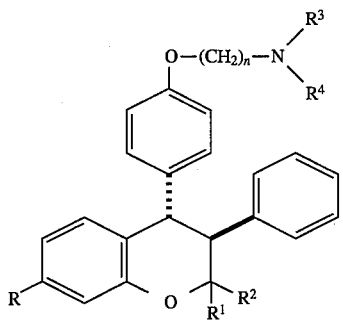

wherein
R is $C_1$–$C_6$ alkyl, $C_1$–$C_6$ alkoxy, halo, or trifluoromethyl;
$R^1$ and $R^2$ each are the same or different $C_1$–$C_6$ alkyl group;
n is an integer from 2 to 6; and
$R^3$ and $R^4$ each are independently $C_1$–$C_4$ alkyl, or combine to form a substituent selected from the group consisting of pyrrolidino, morpholino, piperidino, piperazino, 4-($C_1$–$C_6$ alkyl)piperazino, and 4-phenyl-piperazino;
or a pharmaceutically acceptable salt thereof.

The present invention further relates to methods for inhibiting uterine fibroid disease and endometriosis in women comprising administering to a woman in need of treatment an effective amount of a compound of formula I above, or a pharmaceutically acceptable salt thereof.

DETAILED DESCRIPTION OF THE INVENTION

The present invention concerns methods for lowering serum cholesterol levels, and inhibiting smooth muscle cell proliferation, restenosis, uterine fibroid disease, and endometriosis. The term "inhibit" is defined to include its generally accepted meaning which includes prophylactically treating a subject from incurring one or more of these disease states, holding in check the symptoms of such a disease state, and/or treating such symptoms. Thus, the present methods include both medical therapeutic and/or prophylactic treatment, as appropriate.

The methods of this invention are practiced by administering to an individual in need of treatment an effective amount of a compound of formula I

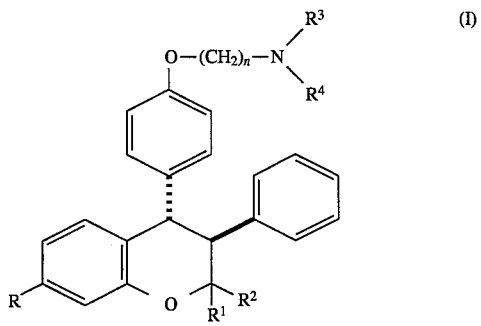

wherein
R is $C_1$–$C_6$ alkyl, $C_1$–$C_6$ alkoxy, halo, or trifluoromethyl;
$R^1$ and $R^2$ each are the same or different $C_1$–$C_6$ alkyl group;
n is an integer from 2 to 6; and
$R^3$ and $R^4$ each are independently $C_1$–$C_4$ alkyl, or combine to form a substituent selected from the group consisting of pyrrolidino, morpholino, piperidino, piperazino, 4-($C_1$–$C_6$ alkyl)piperazino, and 4-phenyl-piperazino;
or a pharmaceutically acceptable salt thereof.

The general chemical terms used in the description of a compound of formula I have their usual meanings. For example, the term "alkyl" by itself or as part of another substituent means a straight or branched aliphatic chain having the stated number of carbon atoms such as, for example, methyl, ethyl, propyl, isopropyl, butyl, pentyl, hexyl, isohexyl, and the like. Likewise, the term "alkoxy" means an alkyl group of the stated number of carbon atoms attached through an oxygen bridge including, for example, methoxy, ethoxy, propoxy, n-propoxy, isopropoxy, and the like.

The term "halo" includes bromo, chloro, fluoro, and iodo.

Compounds of formula I are known in the art and essentially are prepared via the methods described in U.S. Pat. Nos. 3,340,276 and 3,822,287, which are herein incorporated by reference.

U.S. Pat. No. describes, inter alia, the 3,4-diphenylchromans used in the methods of the present invention. However, the process therein disclosed prepares both the less or negligably active cis isomers as well as the substantially more biologically active trans isomers of such compounds. It is preferred, however, to employ the processes disclosed in U.S. Pat. No. 3,822,287 for preparation of the trans isomers which are used in the methods of the present invention.

Preferred formula I compounds include those in which R is alkoxy, especially methoxy, $R^1$ and $R^2$ each are $C_1$–$C_6$ alkyl, especially methyl, n is 2 or 3, especially 2, and $R^3$ and $R^4$ combine to form pyrrolidino, morpholino, and piperidino, especially pyrrolidino. A compound of formula I in which each of the especially preferred substituents is used is known in the art as centochroman.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

Test Procedure

General Preparation Procedure

In the examples illustrating the methods, a post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17α-ethynyl estradiol and the test compound were given orally, unless otherwise stated, as a suspension in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinonoe imine dye, which was read spectrophotemetrically at 500 nm. Cholesterol concentration was then calculated against a standard curve. The entire assay was automated using a Biomek Automated Workstation.

Uterine Eosinophil Peroxidase (EPO) Assay.

Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound

17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below shows comparative results among ovariectomized rats, rats treated with 17α-ethynyl estradiol ($EE_2$, an orally available form of estrogen), and rats treated with a compound of the present invention (centochroman). Although $EE_2$ caused a decrease in serum cholesterol when orally administered at 0.1 mg/Kg/day, it also exerted a stimulatory action on the uterus so that $EE_2$ uterine weight was substantially greater than the uterine weight of ovariectomized test animals. This uterine response to estrogen is well recognized in the art.

Not only did the compound of the present invention substantially reduce serum cholesterol compared to the ovariectomized control animals, but the elevation of uterine weight was less than that observed with $EE_2$. Compared to estrogenic compounds known in the art, the benefit of serum cholesterol reduction without overtly estrogenic effects on uterine weight is quite rare and desirable.

As is expressed in the below data, estrogenicity also was assessed by evaluating the adverse response of eosinophil infiltration into the uterus. The compounds of the present invention caused a moderate increase in the number of eosinophils observed in the stromal layer of ovariectomized rats, while $EE_2$ caused a substantial, expected increase in eosinophil infiltration.

The data presented in the following Table reflects the response of 5 rats per treatment.

TABLE 1

| Compound | Dose mg/kg | Uterine Weight (% increase vs. OVX) | Uterine EPO (V. max) | Serum Cholesterol (% decrease vs. OVX) |
|---|---|---|---|---|
| $EE_2$ | 0.1 | 244.1 | 108.2 | 99.0 |
| Centchroman | 0.1 | 54.1 | 14.4 | 43.7 |
|  | 1.0 | 100.4 | 52.4 | 70.3 |
|  | 10.0 | 79.6 | 60.8 | 54.4 |

In addition to the demonstrated benefits of the compounds used in the methods of the present invention, no deleterious toxicological effects (survival) were observed with any treatment.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Test 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Test 4

A. Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Vascular Smooth Cell Proliferation/Restenosis Test Procedure

Compounds of the present invention have capacity to inhibit vascular smooth cell proliferation. This can be demonstrated by using cultured smooth cells derived from rabbit aorta, proliferation being determined by the measurement of DNA synthesis. Cells are obtained by explant method as described in Ross, *J. of Cell. Bio.* 50:172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181:475–482 (1989).

Inhibition of smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of smooth muscle cell proliferation, particularly restenosis.

For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the methods of the present invention which is capable of lowering serum cholesterol and inhibiting the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.5 mg to about 600 mg/day of a compound of the present invention. Preferred daily doses generally will be from about 15 mg to about 600 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Typically, a formulae compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

Formulations

In the formulations which follow, "active ingredient" means a compound of formula I, or a salt thereof.

| Formulation 1: Gelatin Capsules Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

| Formulation 2: Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

| Formulation 3: Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

We claim:

1. A method for inhibiting endometriosis comprising administering to a woman in need of treatment an effective amount of a compound of formula I

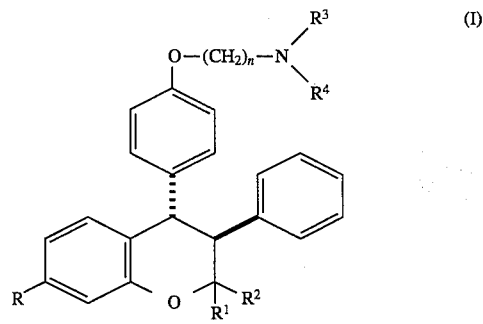

wherein
R is $C_1$–$C_6$ alkyl, $C_1$–$C_6$ alkoxy, halo, or trifluoromethyl;
$R^1$ and $R^2$ each are the same or different $C_1$–$C_6$ alkyl group;
n is an integer from 2 to 6; and
$R^3$ and $R^4$ each are independently $C_1$–$C_4$ alkyl, or combine to form a substituent selected from the group consisting of pyrrolidino, morpholino, piperidino, piperazino, 4-($C_1$–$C_6$ alkyl)piperazino, and 4-phenyl-piperazino;
or a pharmaceutically acceptable salt thereof.

2. A method according to claim 1 wherein the compound of formula I is a compound wherein
R is methoxy;
$R^1$ and $R^2$ each are methyl; and
n is 2;
or a pharmaceutically acceptable salt thereof.

3. A method according to claim 2 wherein the compound of formula I is a compound wherein $R^3$ and $R^4$ combine to form a pyrrolidino group, or a pharmaceutically acceptable salt thereof.

4. A method according to claim 3 wherein said salt thereof is the hydrochloride salt.

* * * * *